United States Patent
Erkamp et al.

(10) Patent No.: US 11,806,187 B2
(45) Date of Patent: Nov. 7, 2023

(54) PASSIVE AND ACTIVE SENSORS FOR ULTRASOUND TRACKING

(71) Applicant: KONINKLIJKE PHILIPS N.V., Eindhoven (NL)

(72) Inventors: Ramon Quido Erkamp, Swampscott, MA (US); Ameet Kumar Jain, Boston, MA (US); Shyam Bharat, Arlington, MA (US); Francois Guy Gerard Marie Vignon, Cambridge, MA (US); Kunal Vaidya, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 260 days.

(21) Appl. No.: 16/468,022

(22) PCT Filed: Dec. 8, 2017

(86) PCT No.: PCT/EP2017/081943
§ 371 (c)(1),
(2) Date: Jun. 10, 2019

(87) PCT Pub. No.: WO2018/108717
PCT Pub. Date: Jun. 21, 2018

(65) Prior Publication Data
US 2020/0008775 A1    Jan. 9, 2020

Related U.S. Application Data
(60) Provisional application No. 62/433,051, filed on Dec. 12, 2016.

(51) Int. Cl.
*A61B 8/08* (2006.01)
*A61B 5/06* (2006.01)
(Continued)

(52) U.S. Cl.
CPC ............ *A61B 8/0841* (2013.01); *A61B 5/065* (2013.01); *A61B 8/4494* (2013.01); *A61B 90/98* (2016.02)

(58) Field of Classification Search
USPC ........................................................ 600/439
See application file for complete search history.

(56) References Cited

U.S. PATENT DOCUMENTS

| 2,238,117 A | 4/1941 | Koch |
| 4,697,595 A | 10/1987 | Breyer et al. |
| (Continued) | | |

FOREIGN PATENT DOCUMENTS

| WO | 2011138698 A1 | 11/2011 |
| WO | 2015121096 A1 | 8/2015 |

OTHER PUBLICATIONS

Merdes, C. L., & Wolf, P. D. (2001). Locating a catheter transducer in a three-dimensional ultrasound imaging field. IEEE Transactions on Biomedical Engineering, 48(12), 1444-1452. (Year: 2001).*

(Continued)

*Primary Examiner* — Jason M Ip
*Assistant Examiner* — Renee C Langhals

(57) ABSTRACT

A system (200) performs a medical procedure in a region of interest of a patient. The system includes an interventional medical device (214) insertable into the region of interest, and a sensor (215) attached to a portion of the interventional device, the sensor being configured to convert an ultrasonic wave from an ultrasound imaging probe (211) to a corresponding electrical radio frequency (RF) signal. The corresponding RF signal is received by a wireless receiver (209) outside the region of interest, enabling determination of a location of the sensor within the region of interest.

6 Claims, 8 Drawing Sheets

(51) Int. Cl.
*A61B 90/98* (2016.01)
*A61B 8/00* (2006.01)

(56) References Cited

U.S. PATENT DOCUMENTS

| | | | | |
|---|---|---|---|---|
| 5,412,619 | A * | 5/1995 | Bauer | G01S 5/26 |
| | | | | 367/128 |
| 6,239,724 | B1 | 5/2001 | Doron | |
| 7,207,941 | B2 | 4/2007 | Sharf | |
| 7,575,550 | B1 * | 8/2009 | Govari | A61B 5/06 |
| | | | | 600/424 |
| 2003/0060700 | A1 | 3/2003 | Solf et al. | |
| 2004/0236193 | A1 * | 11/2004 | Sharf | A61B 5/6882 |
| | | | | 600/302 |
| 2008/0215181 | A1 * | 9/2008 | Smith | A61B 90/36 |
| | | | | 901/30 |
| 2009/0141592 | A1 | 6/2009 | Huang | |
| 2009/0281419 | A1 * | 11/2009 | Troesken | A61B 90/98 |
| | | | | 600/424 |
| 2011/0112403 | A1 * | 5/2011 | Machtey | A61B 8/4477 |
| | | | | 600/443 |
| 2014/0024928 | A1 * | 1/2014 | Boctor | A61B 10/02 |
| | | | | 600/424 |
| 2016/0045184 | A1 | 2/2016 | Courtney | |

OTHER PUBLICATIONS

Härmä, S., & Plessky, V. P. (2009). Surface acoustic wave RFID tags, development and implementation of RFId technology, 145. (Year: 2009).*

Merdes et al: "Locating a Catherter Transducer in a Three-Dimensional Ultrasound Imaging Field"; IEEE Transactions on Biomedical Engineering, vol. 48, No. 12, Dec. 2001, pp. 1444-1452.

PCT/EP2017/081943 ISR and Written Opinion, dated May 18, 2018M 17 Pages.

* cited by examiner

PASSIVE AND ACTIVE SENSORS FOR ULTRASOUND TRACKING

CROSS-REFERENCE TO PRIOR APPLICATIONS

This application is the U.S. National Phase application under 35 U.S.C. § 371 of International Application No. PCT/EP2017/081943, filed on Dec. 8, 2017, which claims the benefit of U.S. Provisional Patent Application No. 62/433,051, filed on Dec. 12, 2016. These applications are hereby incorporated by reference herein.

BACKGROUND

Location tracking of medical devices used in-situ on a patient enables less invasive medical procedures to be carried out. By way of example, ultrasound-guided medical procedures enable the location of certain medical devices relative to a position of interest in a patient.

In certain ultrasound based medical device tracking, electrical wires running from the tip to the handle of the medical device transmit signals to a console/workstation for data analysis.

Among other drawbacks, the connection of the medical instrument to the console/workstation by cables complicates clinical workflow, and introduces undesirable cable management. As a result, the clinical workflow is often impeded because of the presence of cables connecting the medical device to the console. This not only makes it cumbersome for the clinician to perform the procedure, but also limits the market acceptance of such known cable-connected devices and systems.

Accordingly, it is desirable to provide an apparatus, systems, methods, and computer-readable storage media for determining a position of a medical instrument, in-situ, which overcomes at least the short-comings of the above-described known devices.

BRIEF DESCRIPTION OF THE DRAWINGS

The present invention will be more readily understood from the detailed description of representative embodiments presented below considered in conjunction with the accompanying drawings, as follows.

DETAILED DESCRIPTION

Figure 1A:
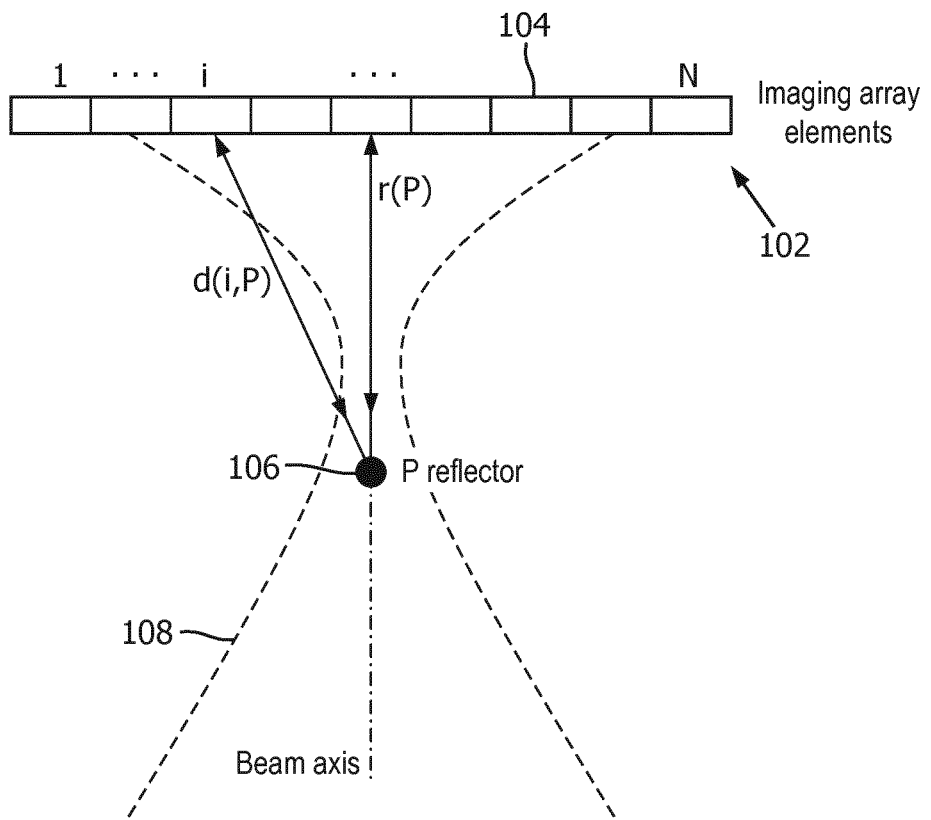
FIG. 1A is a conceptual diagram depicting two-way ultrasound signal transmission, in accordance with a representative embodiment.

The present teachings are described hereinafter with reference to the accompanying drawings, in which representative embodiments are shown. The present teachings may, however, be embodied in different forms and should not be construed as limited to the embodiments set forth herein. Rather, these embodiments are provided as teaching examples.

Generally, according to various embodiments, is to be understood that the terminology used herein is for purposes of describing particular embodiments only, and is not intended to be limiting. Any defined terms are in addition to the technical and scientific meanings of the defined terms as commonly understood and accepted in the technical field of the present teachings.

As used in the specification and appended claims, the terms "a", "an" and "the" include both singular and plural referents, unless the context clearly dictates otherwise. Thus, for example, "a device" includes one device and plural devices.

Unless otherwise noted, when an element or component is said to be "connected to," "coupled to" another element or component, it will be understood that the element or component can be directly connected, directly coupled to the other element or component, or, intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

Also, it will be understood that, in addition to their ordinary meanings, the terms "substantial" or "substantially" mean to within acceptable limits or degree to one having ordinary skill in the art. For example, "substantially cancelled" means that one of ordinary skill in the art would consider the cancellation to be acceptable. Likewise, in addition to its ordinary meaning, the term "approximately" means to within an acceptable limit or amount to one having ordinary skill in the art. For example, "approximately the same" means that one of ordinary skill in the art would consider the items being compared to be the same.

Directional terms/phrases and relative terms/phrases may be used to describe the various elements' relationships to one another, as illustrated in the accompanying drawings. These terms/phrases are intended to encompass different orientations of the device and/or elements in addition to the orientation depicted in the drawings.

Like numbered elements in these figures are either equivalent elements or perform the same function. Elements which have been discussed previously will not necessarily be discussed in later figures if the function is equivalent.

Initially, it is noted that medical images may include 2D or 3D images such as those obtained using an ultrasound probe, and a position of a medical instrument relative to an image frame of ultrasound signals from the ultrasound probe.

In accordance with a representative embodiment, an apparatus for performing a medical procedure is disclosed. The apparatus comprises; a sensor adapted to convert an ultrasonic signal incident thereon into an electrical signal; and a wireless transceiver configured to receive the electrical signal from the sensor, and to transmit the electrical signal to a wireless receiver remote from the apparatus.

In accordance with another representative embodiment, an ultrasound system, comprises: an ultrasound probe adapted to insonify a region of interest; an apparatus configured to perform a medical procedure, the apparatus comprising: a sensor adapted to convert an ultrasonic signal incident thereon into an electrical signal; and a first wireless transceiver configured to transmit the electrical signal; and a control unit remote from the ultrasound probe and apparatus. The control unit is adapted to provide an image from the ultrasound probe. The control unit comprises: a second wireless transceiver configured to receive the electrical signal from the first wireless transceiver, and a processor adapted to overlay the position of the apparatus on the image.

Figure 1B:
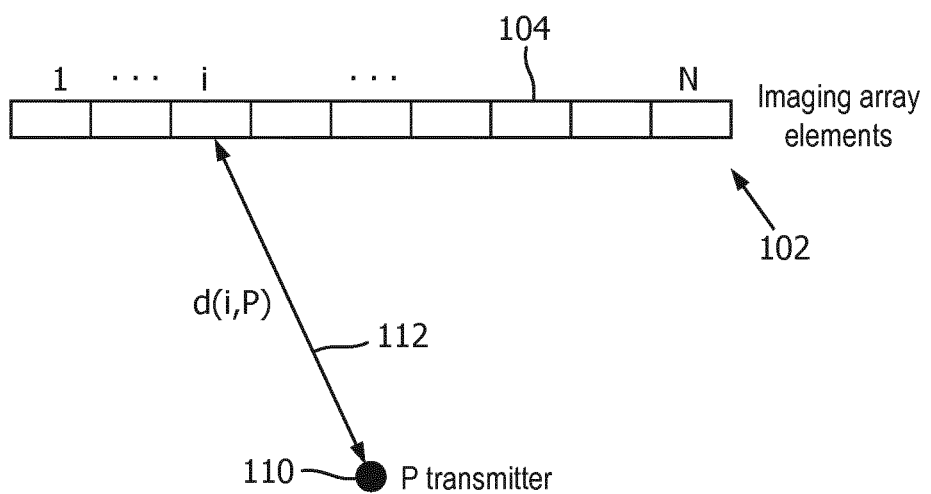
FIG. 1B is a conceptual diagram depicting one-way ultrasound signal transmission, in accordance with a representative embodiment.

FIGS. 1A and 1B offer, by way of an illustrative and non-limitative example, a comparison between two-way beamforming (FIG. 1A) and one-way only beamforming (FIG. 1B).

Turning to FIG. 1A, representative of two-way beamforming shows an imaging array 102 of N elements 104 issuing ultrasound signals that impinge on a reflector 106. Since the ultrasound waves go out and back (from the imaging array to the reflectors and back to the imaging array), this beamforming is "two-way" or "round-trip" beamforming. On receiving (of the ultrasound that has reflected back), beamforming determines the reflectivity of the reflector 106 and the position of the reflector relative to the array 102. The array 102 sends out an ultrasound beam 108 that is reflected from the reflector 106 and returns to all elements 104 of the array 102. The flight of the beam is over a distance r(P)+d(i,P) for element i. Each element 104 measures continually the amplitude of the return ultrasound. For each element 104, the time until a maximum of that measurement, i.e., the "round-trip time of flight," is indicative of the total flight distance. Since the r(P) leg of the flight is constant, the return flight distance d(i,P) is determined. From these measurements, the relative position of the reflector 106 is computed geometrically. As to the reflectivity of the reflector 106, it can be indicated by summing the maxima over all i (i.e., over all elements 104). Notably, beamforming, a geometrical computation, not only takes place in receive mode but also in transmit mode. As such a beamformer (e.g., beamformer 210 described in connection with FIG. 2) in transmit mode sends properly delayed signals to all the elements 104 (and generates the frame and line trigger signals), and in receive mode properly delays and sums the signals from the individual elements 104.

When imaging tissue, there may be many reflectors with varying reflection magnitudes, respectively. To find tissue reflection intensity at a particular location, the geometrical element delays for that location are calculated and the shifted signals are summed. These delays vary dynamically in time as the whole imaging frame is being constructed, in a process referred to as dynamic receive beamforming. For tracking of the instrument, data may be recorded with a sensor at the device location, and the timing of frame and line triggers may also be recorded.

Turning to FIG. 1B, one-way only (receive) beamforming is depicted. Notably, as the name implies, in one-way beamforming there is echo, but it is not used. Instead, an ultrasound transmitter 110 emits an ultrasound beam 112, which is incident on each element 104 of the array 102. The flight here, in contrast to the two-way beamforming case, is over the distance d (i,P). The time from emission of the ultrasound beam 112 until the maximum amplitude reading at an element 104 determines the value d (i,P) for that element i. Thus, the position of the ultrasound transmitter 110 can be derived geometrically, and the reflectivity calculated by summing the maximum amplitude readings.

Although one-way beamforming is implementable in the time domain via delay logic, as discussed hereinabove, it can also be implemented in the frequency domain by well-known Fourier beamforming algorithms.

As will become clearer as the present description continues, two-way beamforming is used to gather images on a frame-by-frame basis; and one-way beamforming is used to determine the location of a sensor disposed at a known position on a medical device (sometimes referred to generically as an apparatus). For example, the sensor could be attached at or near (e.g., about 1 mm away from) the tip (or distal end) of a needle or other medical device.

Figure 2:
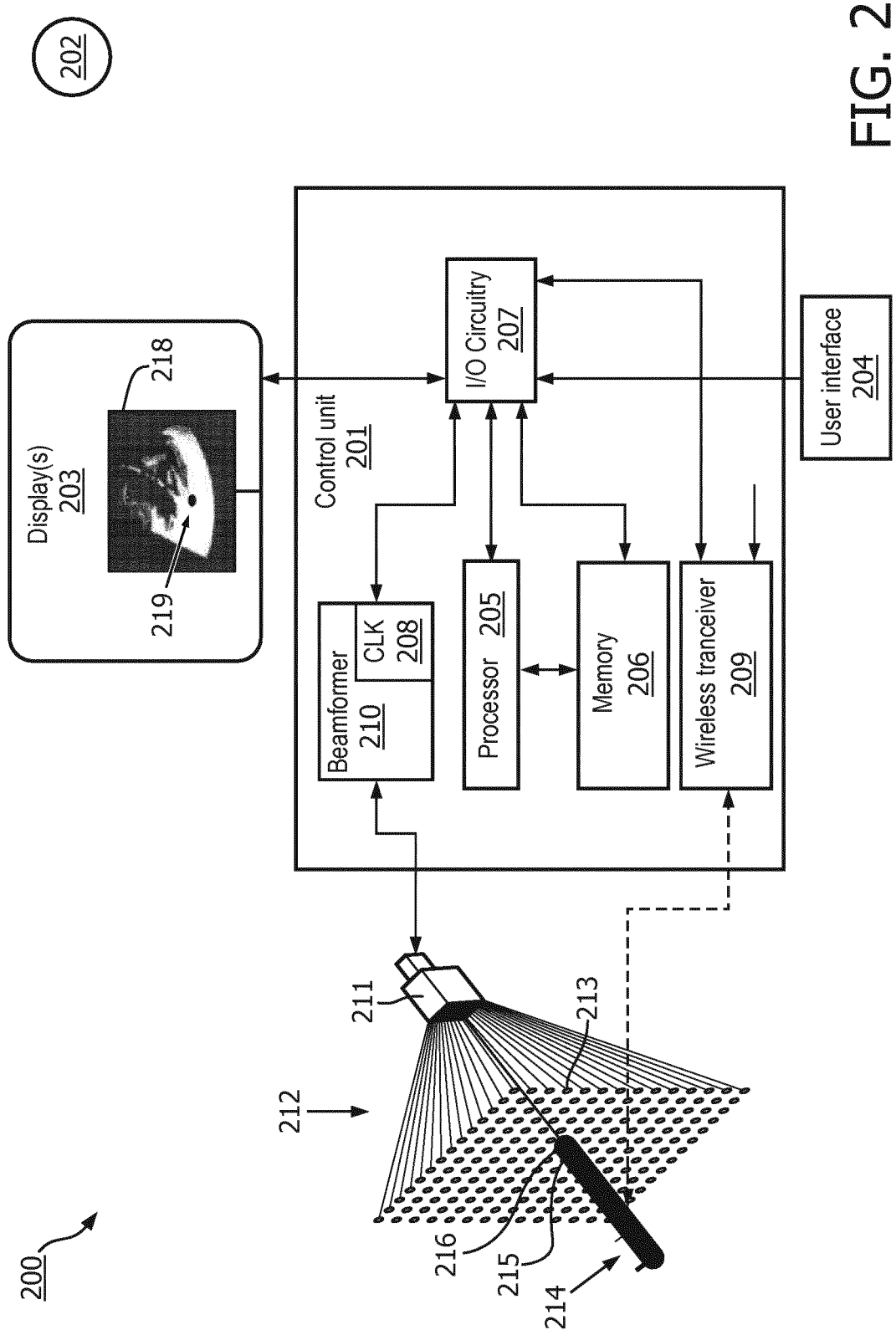
FIG. 2 is a schematic block diagram showing an ultrasound system, in accordance with a representative embodiment.

FIG. 2 is a simplified schematic block diagram showing an ultrasound system 200, in accordance with a representative embodiment of the present invention. The ultrasound system 200 comprises a number of components, the functions of which are described more fully below.

The ultrasound system comprises a control unit 201, which is connected to a display 203, and a user interface 204. The control unit 201 comprises a processor 205, which is connected to a memory 206, and input output (I/O) circuitry 207. The control unit 201 further comprises a clock (CLK) 208 (sometimes referred to below as a first clock), which provides clock signals, to the I/O circuitry for distribution to and use in the ultrasound system 200, as described more fully below. As will become clearer as the present description continues, the clock 208 is substantially synchronized with a clock (not shown) of a medical device 214 to ensure substantial simultaneity of frame and trigger signals provided by the control unit 201 during a scan.

The control unit 201 also comprises a wireless transceiver 209, which is adapted to connect to various components of the ultrasound system 200, such as a wireless network 202, and others as described more fully below.

Finally, the control unit 201 comprises a beamformer 210. The beamformer 210 is adapted to receive signals from an ultrasound imaging probe 211. As described more fully below, the ultrasound imaging probe 211 is adapted to scan the region of interest 212, and provides images on a frame-by-frame basis.

The ultrasound system 200 also comprises the medical device 214, which comprises a sensor 215 (see FIGS. 3 and 4 for more detail) disposed at or near (a known distance from) a distal end 216 of the medical device 214. The distal end 216 is disposed at a target location in the region of interest 212.

As described more fully below, the sensor 215 is adapted to convert ultrasound beams provided by the ultrasound imaging probe 211 into electrical signals, and to provide either the raw data from the sensor 215, or partially or completely processed data (e.g., calculated sensor location) from the sensor 215, to the control unit 201 via the wireless transceiver, either directly or indirectly (e.g., via a transmitter or repeater located in a proximal end of the medical device 214). These data, depending on their degree of processing, are either used by the control unit 201 to determine the location of the distal end 216 of the medical device 214, or provide to the control unit 201 the location of the distal end 216 of the medical device 214.

As will become clearer as the present description continues, the control unit 201 is illustratively a computer system, which comprises a set of instructions that can be executed to cause the control unit 201 to perform any one or more of the methods or computer based functions disclosed herein. The control unit 201 may operate as a standalone device (e.g., as the computer of a stand-alone ultrasound system), or may be connected, for example, using a wireless network 202, to other computer systems or peripheral devices. Generally, connections to the wireless network 202 are made using a hardware interface, which is generally a component of I/O circuitry 207, which is described below.

In accordance with a representative embodiment, the display 203 is an output device and/or a graphical user interface adapted for displaying images or data. A display may output visual, audio, and or tactile data. The display 203 may be, but is not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display, for example.

The user interface 204 allows a clinician or other operator to interact with the control unit 201, and thereby with the ultrasound system 200. The user interface 204 may provide information or data to the operator and/or receive information or data from the clinician or other operator, and may enable input from the clinician or other operator to be received by the control unit 201 and may provide output to the user from the control unit 201. In other words, the user interface 204 may allow the clinician or other operator to control or manipulate the control unit, and may allow the control unit 201 to indicate the effects of the control or manipulation by the clinician or other operator. The display of data or information on the display 203 or graphical user interface is an example of providing information to an operator. The receiving of data through a touch screen, keyboard, mouse, trackball, touchpad, pointing stick, graphics tablet, joystick, gamepad, webcam, headset, gear sticks, steering wheel, wired glove, wireless remote control, and accelerometer are all examples of user interface components which enable the receiving of information or data from a user.

The user interface 204, like the display 203 are illustratively coupled to the control unit 201 via a hardware interface (not shown) and the I/O circuitry 207 as would be appreciated by those skilled in the art. The hardware interface enables the processor 205 to interact with various components of the ultrasound system 200, as well as control an external computing device (not shown) and/or apparatus. The hardware interface may allow the processor 205 to send control signals or instructions to various components of the ultrasound system 200, as well as an external computing device and/or apparatus. The hardware interface may also enable the processor 205 to exchange data with various components of the ultrasound system, as well as with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

In a networked deployment, the control unit 201 may operate in the capacity of a server or as a client user computer in a server-client user network environment, or as a peer control unit in a peer-to-peer (or distributed) network environment. The control unit 201 can also be implemented as or incorporated into various devices, such as a stationary computer, a mobile computer, a personal computer (PC), a laptop computer, a tablet computer, a wireless smart phone, a set-top box (STB), a personal digital assistant (PDA), a global positioning satellite (GPS) device, a communications device, a control system, a camera, a web appliance, a network router, switch or bridge, or any other machine capable of executing a set of instructions (sequential or otherwise) that specify actions to be taken by that machine. The control unit 201 can be incorporated as or in a particular device that in turn is in an integrated system that includes additional devices. In a representative embodiment, the control unit 201 can be implemented using electronic devices that provide voice, video or data communication. Further, while a single control unit 201 is illustrated, the term "system" shall also be taken to include any collection of systems or sub-systems that individually or jointly execute a set, or multiple sets, of instructions to perform one or more computer functions.

The processor 205 for the control unit 201 is tangible and non-transitory. As used herein, the term "non-transitory" is to be interpreted not as an eternal characteristic of a state, but as a characteristic of a state that will last for a period of time. The term "non-transitory" specifically disavows fleeting characteristics such as characteristics of a particular propagating carrier wave or signal or other forms that exist only transitorily in any place at any time.

The processor 205 is an article of manufacture and/or a machine component. As described more fully below, the processor 205 is configured to execute software instructions in order to perform functions as described in the various representative embodiments herein. The processor 205 may be a general purpose processor or may be part of an application specific integrated circuit (ASIC). The processor 205 may also be a microprocessor, a microcomputer, a processor chip, a controller, a microcontroller, a digital signal processor (DSP), a state machine, or a programmable logic device. The processor 205 may also be a logical circuit, including a programmable logic device (PLD) such as a programmable gate array (PGA), a field programmable gate array (FPGA), or another type of circuit that includes discrete gate and/or transistor logic. The processor 205 may be a central processing unit (CPU), a graphics processing unit (GPU), or both. Additionally, the processor 205 may include multiple processors, parallel processors, or both. Multiple processors may be included in, or coupled to, a single device or multiple devices of the ultrasound system 200.

The memory 206 is an article of manufacture and/or machine component, and is a computer-readable medium from which data and executable instructions can be read by a computer. The memory 206 may include one or more of random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

Generally, the memory 206 comprises a tangible storage medium that can store data and executable instructions, and are non-transitory during the time instructions are stored therein. Further, the instructions stored in memory 206, when executed by the processor 205, can be used to perform one or more of the methods and processes as described herein. In a particular embodiment, the instructions may reside completely, or at least partially, within the memory 206. Notably, the instructions may reside within the processor 205 during execution by the control unit 201.

In accordance with a representative embodiment described below in connection with FIGS. 3A-4B, the position of the sensor 215 is determined by the medical device 214 and transmitted to the control unit 201 via the wireless transceiver 209. Using the position of the sensor 215 provided, the processor 205 executes instructions stored in memory 206 to overlay the position of the sensor 215 an image frame, and thus the distal end 216 of the medical device 214 relative to the image of each frame. In another representative embodiment, the instructions stored in memory 206 are executed by the processor 205 to determine a position of the sensor 215 in an image frame, and to overlay the position of the sensor 215, and thus the distal end 216 of the medical device 214 relative to the image of each frame. One illustrative method of determining the position of the distal end 216, for which instructions are stored in memory 206 is described below in connection with FIGS. 4A and 4B.

Alternatively, in accordance with a representative embodiment, and as alluded to above, dedicated hardware implementations, such as application-specific integrated circuits (ASICs), programmable logic arrays and other hardware components, can be constructed to implement one or more of the methods and processes described herein. One or more representative embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware-based control unit 201 that executes software programs. Further, in a representative embodiment, implementations can include distributed processing, component/object distributed processing, and parallel processing. Virtual computer system processing can be constructed to implement one or more of the methods or functionality as described herein, and the processor 205 described herein may be used to support a virtual processing environment.

The present teachings contemplate a computer-readable medium that includes instructions, or receives and executes instructions responsive to a propagated signal; so that a device connected to the wireless network 202 can communicate voice, video or data over the wireless network 202. Further, the instructions may be transmitted or received over the wireless network 202 via a network interface device (not shown).

The wireless transceiver 209 is contemplated to be a radio frequency (RF) transceiver, or an optoelectronic transceiver. As described more fully below, the medical device 214 comprises a transceiver adapted to communicate with the wireless transceiver, and thus may be an RF transceiver or an optoelectronic transceiver, depending on the components of the wireless transceiver. The wireless transceiver 209 thus comprises at least an antenna, multiplexing/demultiplexing components, amplifiers and filters as needed to transmit and receive data to and from the medical device 214.

The I/O circuitry 207 receives inputs from various components of the ultrasound system 200, and provides output to and receives inputs from the processor 205, as is described more fully below. I/O circuitry 207 controls communication to elements and devices external to the control unit 201. The I/O circuitry 207 acts as an interface including necessary logic to interpret input and output signals or data to/from the processor 205. The I/O circuitry 207 is configured to receive the acquired live images from the beamformer 210, for example, via a wired or wireless connection. The I/O circuitry 207 is also configured to receive data from the medical device 214. As described more fully below, the I/O circuitry 207 provides these data to the processor 205 to ultimately superpose the location of the distal end 216 of the medical device 214 in a particular image frame.

Broadly, in operation, based on input from the user interface 204 provided to the processor 205 by the I/O circuitry 207, the processor 205 initiates a scan by the ultrasound imaging probe 211. The scan launches ultrasound waves across the region of interest 212. The ultrasound waves are used to form an image of a frame by the beamformer 210; and to determine the location of the sensor 215 of the medical device 214. As can be appreciated, the image is formed from a two-way ultrasound transmission sequence, with images of the region of interest being formed by the transmission and reflection of sub-beams by plurality of transducers. By contrast, these sub-beams are incident on the sensor 215, which converts the ultrasound signals into electrical signals in a one-way ultrasound method. As described below in connection with FIGS. 4A and 4B, based on frame and line trigger signals generated in beamformer 210 and via the wireless transceiver 209 provided to the medical device 214, the location of the sensor 215 is determined.

While images in the region of interest 212 are being garnered by the ultrasound imaging probe 211, one-way data is garnered by the sensor 215. As noted above, and as described more fully below, these data may comprise raw data, partially processed data, or fully processed data. Depending on the degree of processing, these data can be provided to the processor 205 for executing instructions stored in the memory 206 to determine the position of the sensor 215 in the coordinate system of ultrasound images from the beamformer 210; or may include the determined position of the sensor 215 in the coordinate system which is used by the processor when executing instructions stored in the memory 206 to overlay the position of the sensor 215 on the ultrasound image in the coordinate system thereof. To this end, the beamformer 210 processes the beamformed signal for display as an image of a frame. The output from the beamformer 210 can be provided to the processor 205. The data from the sensor 215 may be raw data, in which case the processor 205 executes instructions in the memory 206 to determine the position of the sensor 215 in the coordinate system of the image; or the data from the sensor 215 may be processed by the medical device to determine the location of the sensor 215 in the coordinate system of the image. Either way, the processor 205 is configured to overlay the position of the sensor 215 in a particular frame on the image from the beamformer 210 from that frame. A composite image 218, comprising the image of the frame from the ultrasound imaging probe 211 and the superposed position 219 of the sensor 215 in that frame is provided on the display 203 providing real-time feedback to a clinician of the position of the distal end 216 of the medical device 214 relative to the region of interest 212. As can be appreciated, the superposing of the position of the sensor 215 is repeated for each frame to enable complete real-time in-situ superposition of the position of the sensor 215 relative to the composite image 218 of the particular frame.

Figure 3A:
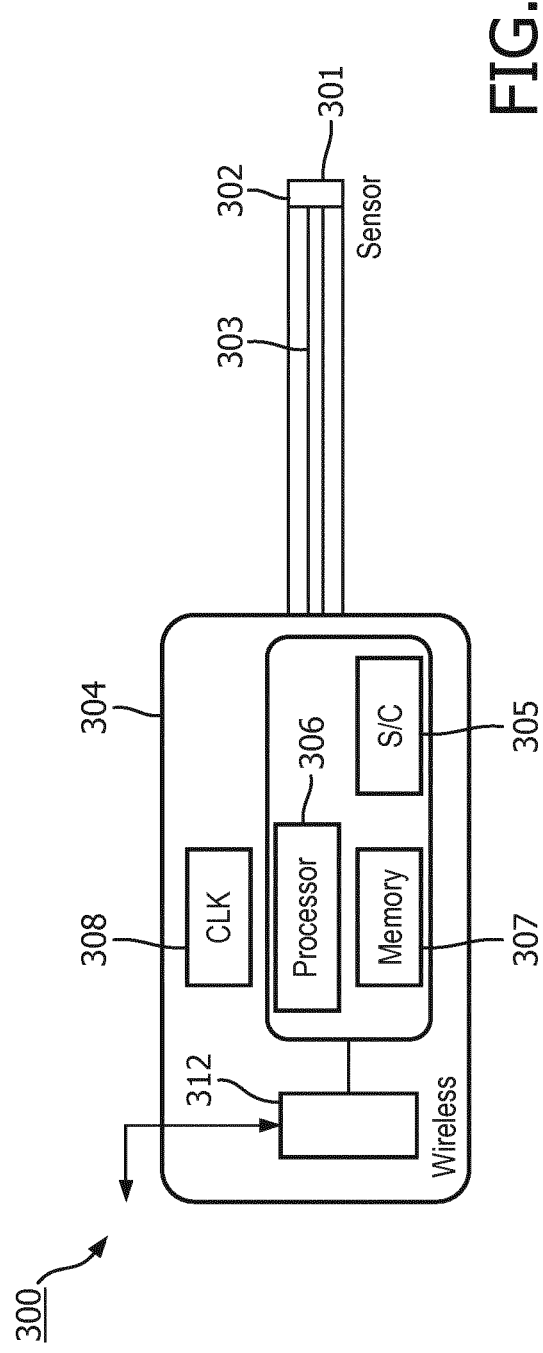
FIG. 3A is a simplified schematic block diagram showing a medical device, in accordance with a representative embodiment.

FIG. 3A is a simplified schematic block diagram showing a medical device 300, in accordance with a representative embodiment. Many details of the medical devices described above in connection with FIGS. 1A-2 are common to the details of medical device 300, and may not be repeated in the description of the medical device 300.

The medical device 300 is contemplated to be any one of a number of medical devices where the location of a distal end relative to a position in a region of interest, including but not limited to a needle, such as a biopsy or therapeutic needle, or a medical instrument, such as a laparoscope, or a scalpel, is desired. It is emphasized that the listed medical devices are merely illustrative, and other medical devices that benefit a clinician through the determination of their distal ends are contemplated.

Turning to FIG. 3A, the medical device 300 comprises a sensor 302 disposed at or near (a known distance from) a distal end 301. As described above, the sensor 302 is an ultrasonic sensor adapted to convert ultrasonic (mechanical) waves incident thereon into electrical signals. In a representative embodiment, the sensor comprises a piezoelectric element, such as a thin film piezoelectric material, or a piezoceramic material. Upon incidence of an ultrasound signal, the sensor effects the conversion, and electrodes (not shown) connected to the sensor 302 transmit the electrical signal through electrical or optical conductors 303 to a hub 304. The hub 304 may be for example, the handle of the medical device 300, which is disposed at the proximal end of the medical device 300.

After processing of the electrical signal from the sensor 302, as described above and below, a wireless transceiver 312 transmits the processed electrical signal to a console (e.g., control unit 201) remote from the medical device 300. As noted above, depending on the type of wireless transceiver at the console (e.g., wireless transceiver 209 of control unit 201), the wireless transceiver 312 may be an RF transceiver or an optoelectronic transceiver, for example, adapted to transmit and receive data from the console, although other transceivers may be incorporated without departing from the scope of the present teachings.

By way of example, the wireless connection between the wireless transceiver 312 and the wireless transceiver at the console may be configured to operate under a known wireless protocol, including, but not limited to Zigbee, Bluetooth, or Wi-Fi, and include the necessary components to effect the layer structure of the protocol. Alternatively, the wireless connection may be implemented using a proprietary protocol.

Moreover, an optical link may be used to effect the wireless connection. Just by way of example, in accordance with a representative embodiment, two narrow band light emitters (i.e. a red and a green LED) may be used to effect the wireless connection. Illustratively, a 128 bit pulse sequence can be created with a red flash representing a "0", and a green flash representing a "1" to transmit a 128 bit number. Error correcting coding such as Reed-Solomon can be used to have more robust transmission.

In the presently described representative embodiment, the medical device 300 comprises a signal conditioning module 305, a processor 306, and a memory 307. Notably, the processor 306 and memory 307 may comprise the same or similar structure and composition of the processor 205 and memory 206 described above.

The medical device 300 also comprises a clock 308 (sometimes referred to as a second clock), which is substantially synchronized with the clock of the console (e.g., clock 208 depicted in FIG. 2). As described more fully below in connection with FIGS. 4A-4B, the timing of frame and line trigger signals received from the console/control unit, are used to determine the location of the sensor 302. As such, the substantial synchronization of the clock 308 and the remote clock (e.g., clock 208) is useful in ensuring the determination of the timing, and thereby the location, of the sensor 302 relative to a scanned image of a particular frame.

Figure 3B:
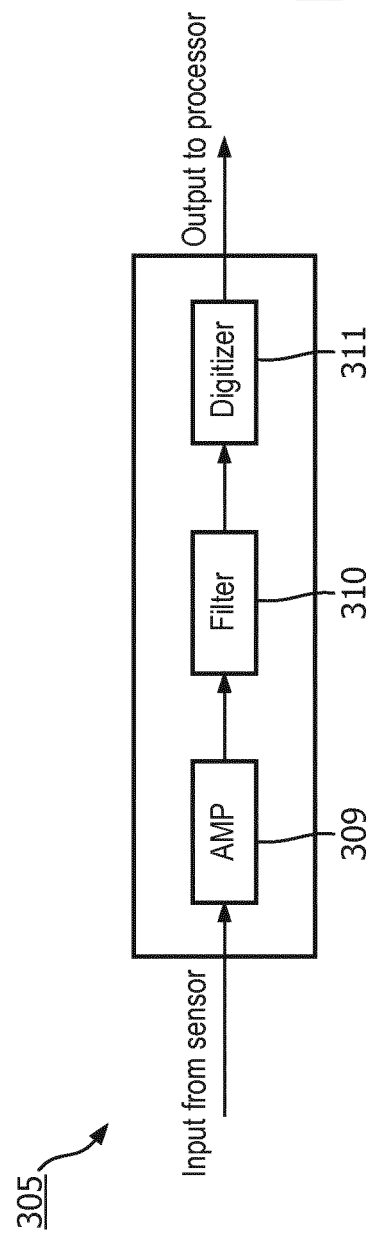
FIG. 3B is a simplified schematic diagram showing a medical device, in accordance with another illustrative embodiment of the present invention.

As shown in FIG. 3B, the signal conditioning module 305 comprises an amplifier 309, a filter 310, and a digitizer 311. The amplifier 309 and filter 310 may be one of a number of known components useful in amplifying and filtering an electrical signal to provide a desired minimum signal to noise ratio (SNR). The digitizer 311 may be a known digitizer, such as an analog to digital (A/D) converter commonly used in RF or optical communications, depending on the chosen medium for transmission between the medical device 300 and the remote console.

In accordance with a representative embodiment, the amplifier 309 may be optimized for the acoustic sensor 302 and include features such as charge amplification and balanced inputs with high common mode signal rejection, or if the sensor is optoacoustic in nature, include for example a photo-transistor. The filter 310 may be a simple analog bandpass filter, an analog envelope detector with RF carrier frequency demodulation, or may contain a nonlinear resonant structure that is highly sensitive to specific waveform patterns. The digitizer 311 may sample at rates suitable for raw RF signals, or a lower rate sufficient for proper RF envelope sampling. To optimize dynamic range, nonlinear quantization steps (such as LOG scale) may be used, and/or the digitizer reference voltage may be based on recently measured signal amplitudes or change in time (TGC).

An input signal from the sensor 302 is received through the electrical or optical conductors 303 at the amplifier 309, where it is amplified to a suitable level, and transmitted to the filter 310. After receipt from the filter 310, the signal is digitized by the digitizer 311, and provided to the processor 306 (see FIG. 3A).

The memory 307 comprises a tangible storage medium that can store data and executable instructions, and are non-transitory during the time instructions are stored therein. The instructions stored in memory 307 are executed by the processor 306 to determine a position of the sensor 302 in each image frame. One illustrative method of determining the position of the distal end 301, for which instructions are stored in memory 307 is described below in connection with FIGS. 4A and 4B.

As described above, the electrical signal transmitted from the wireless transceiver 312 may be partially or completely processed prior to transmission to a remote wireless transceiver (e.g., wireless transceiver 209 of control unit 201). In the presently described embodiment, the signal from the sensor 302 is used to determine the location of the distal end 301. This location is then transmitted to the remote control unit, where it is used to overlay the position of the distal end 301 real time, as noted above.

One method for determining the location of the distal end comprises collecting/storing the signal from the sensor 302 over the duration of a complete frame, then find the time at clock 308 where maximum signal is received (again, the clock 308 is synchronized using the frame and line triggers that are wirelessly received). As the beam transmit parameters are known, this clock time can then be used to either mathematically calculate the position or find the position in a lookup table stored in memory 307, for example. The calculation/lookup could take place in the medical device 300, and coordinates transmitted to the remotely located control unit 201, or the clock time from clock 308 could be transmitted and calculation/lookup performed in control unit 201.

In an alternative embodiment, the processor 306, clock 308, and memory 307 are not provided in the medical device 300, and only partially processed data is transmitted by the wireless transceiver 312 to the control unit. The sensor signal is now transmitted (e.g., continuously) through a channel that has a fixed and known latency. In the present example, partially processed data comprises the amplified and filtered signal that can be either kept analog or optionally can be digitized and provided at the output of the signal conditioning module 305. These data are provided to the wireless transceiver 312, and transmitted to the remote console/control unit. As described above, in this latter embodiment, the control unit comprises a processor (e.g., processor 205) and memory (e.g., memory 206) useful in determining the position of the sensor 302 and thus distal portion; and is adapted to overlay the determined position on an image from a scan real-time. The timing of the detected maximum sensor signal is known due to the fixed/known latency of the wireless transmit channel, and line and frame trigger signals are available from the beamformer (e.g., beamformer 210) in transmit mode.

Notably, as part of processing, the signal from the sensor 302 may be clipped to include only the relevant parts of the signal (e.g., in and around the maximum signal intensity location as described below in connection with FIGS. 4A and 4B) for each frame. Furthermore, the signal of only the ultrasound beam incident on the sensor 302 with the maximum signal may be transmitted (along with other information such as timing and encoding parameters). Beneficially, these methods are aimed at reducing the size of the data packet before transmission from the wireless transceiver 312, thereby allowing for easier transmission from the medical device 300 to the console.

Figure 4A:
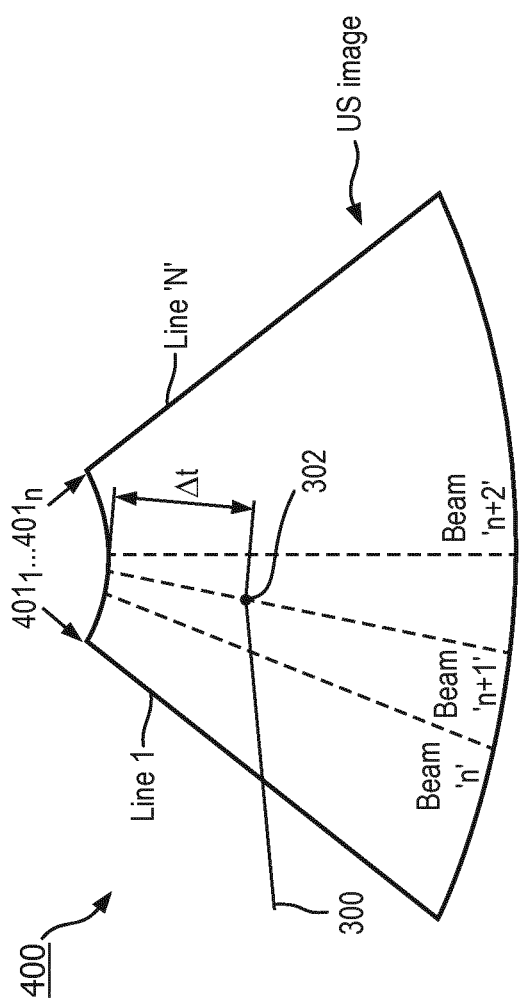
FIG. 4A is a conceptual diagram depicting a frame scan using a plurality of ultrasound beams.

FIG. 4A is a conceptual diagram depicting a frame scan 400 using a plurality of ultrasound beams of an ultrasound system of a representative embodiment. FIG. 4B shows the relative timing of frame trigger signals, line trigger signals, and a received sensor signal of a medical device in accordance with a representative embodiment. Many details of the medical devices described above in connection with FIGS. 1A-3B are common to the details of the conceptual diagram and timing diagram of FIGS. 4A-4B, and may not be repeated in their description.

Turning to FIG. 4A, medical device 300 having sensor 302 at or near (a known distance from) a distal end is provided in proximity in-situ to a region of interest in a body, for example. A plurality of ultrasound transducers $401_1$-$401_N$ each generates respective ultrasound beams (beams 1-beam N) in a scan across the region of interest. As shown in FIG. 4B, frame trigger (e.g., First Frame), which is provided at the beginning of a scan, results in scanning over the region of interest to provide an image frame. As is known, the scanning is sequential from ultrasound transducer $401_1$ through $401_N$, and at the next frame, the sequence is repeated to generate the next image frame (Frame 2). Moreover, each ultrasound beam (beams 1-beam N) is triggered by a respective line trigger, with each successive beam being terminated at the reception of the next line trigger.

Figure 4B:
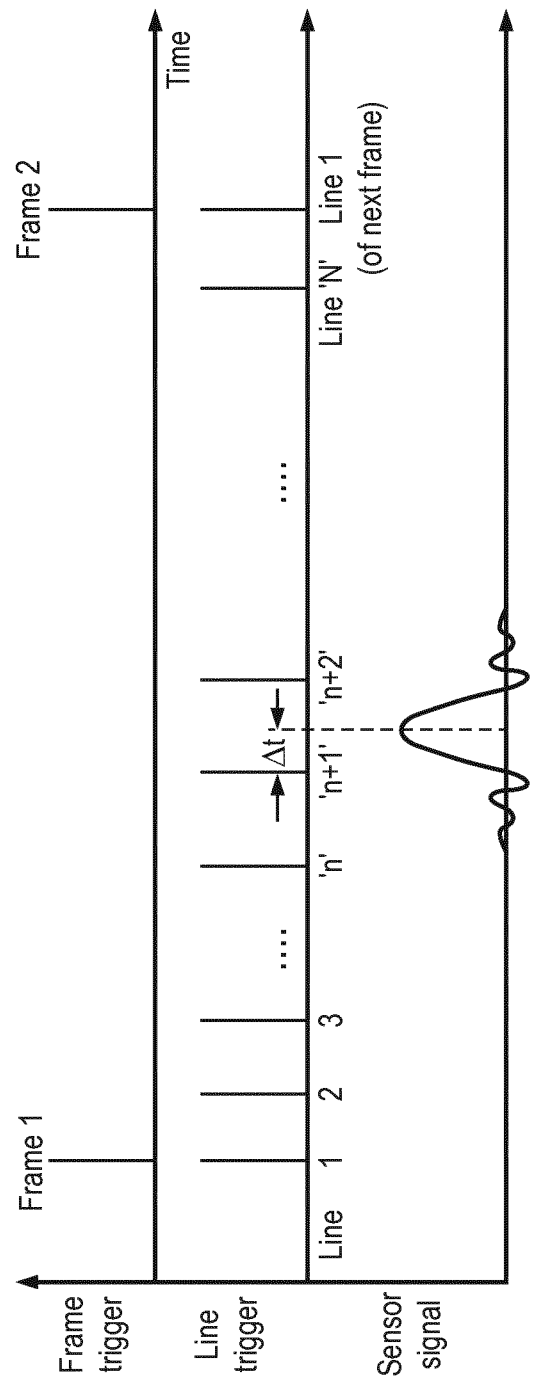
FIG. 4B shows the relative timing of frame trigger signals, line trigger signals, and a received sensor signal of a medical device in accordance with a representative embodiment.

As depicted in FIGS. 4A and 4B, a first frame scan (Frame 1) begins with a frame trigger, with the first ultrasound transducer $401_1$ being excited at the first line trigger (Line 1). Next, the second ultrasound transducer 402 is excited at the second line trigger (Line 2). As noted above this sequence continues until the end of the first frame at which point the second frame scan (Frame 2) begins with the second frame trigger, which coincides with the first line trigger of the second/next frame. The sequence begins anew by the exciting of the first ultrasound transducer $401_1$ at the first line trigger (Line 1); followed by the second ultrasound transducer 402 at the second line trigger (not shown) of the second frame; and so forth until the termination of the second frame.

As can be seen in FIGS. 4A and 4B, a signal is received at the sensor 302 at a time coinciding with the line trigger n+1, with a maximum amplitude being received at a time Δt along the line n+1. As described presently, this signal is used to determine the location of the sensor 302 relative to the first frame, and is superposed on the image of the frame, and thereby at a particular coordinate (x,y) of the coordinate system of the first frame image (e.g., composite image 218, comprising the image of the frame from the ultrasound imaging probe 211 and the superposed position 219 of the sensor). That is, for example, when performing 2D imaging, all sensor data is collected for one frame, timing of maximum sensor signal over that frame is determined, the sensor position is calculated after the last beam of the frame, and then the frame is displayed and the sensor location is drawn on the frame. In 3D imaging, all data for the volume is first collected, then that volume is rendered and the sensor position is annotated in that volume.

In a first representative embodiment, and as noted above, the position of the sensor in the coordinate system of the first frame is determined at the processor of the console/control unit (e.g., processor 205). In such an embodiment, the medical device 300 transmits the data from the sensor to the console/control unit that is remotely located. These data are provided to the processor (e.g., processor 205), and the instructions stored in memory (e.g., memory 206) are executed by the processor to determine a position of the sensor 302 in an image frame, and to overlay the position of the sensor 302, and thus the distal end of the medical device 300 relative to the image of the first frame.

As noted above the first and second clocks 208, 308 are substantially synchronized with respect to each other. The first and second clocks 208, 308 can be one-time synchronized, synchronized before every procedure, or synchronized whenever time settings on the ultrasound probe are changed or intermittently, as desired. Alternatively, the frame and line triggers that are derived from clock 208 can be transmitted to the medical device and used to synchronize clock 308. A one-time constant synchronization may be sufficient in many cases, depending on the quality of the clocks and time duration of medical device use.

In the present embodiment, the beamformer 210 provides frame and line trigger signals. Every time a frame trigger signal or a line trigger is raised, it is transmitted from the console/control unit (e.g., control unit 201) via the wireless transceiver (e.g., wireless transceiver 209) to the medical device 300. Alternatively one could also transmit only the frame triggers or a predetermined subset (e.g., odd, even, every fifth, etc.) of the line triggers. Both the medical device 300 and the console/control unit store the clock time of the respective trigger signals.

When the processor 306 on the medical device 300 detects a relevant signal from the sensor 302, it parses the signal, making it ready for transmission. The processor 306 is adapted to assign a time of reception of the signal from the sensor 302 that is stored in the memory 307. The medical device then transmits the signal data and the time of the sensor signal to the console/control unit wirelessly (i.e., via the wireless transceiver 312 and the wireless transceiver 209). So, in the present representative embodiment, the sensor signal having a peak magnitude at time $\Delta t$ relative to line trigger n+1 is transmitted from the medical device 300 to the console/control unit, where its processor (e.g., processor 205) using instructions from the memory 206 determines the location of the sensor relative to the image of the first frame.

As can be appreciated, because the timing of the frame and line triggers are transmitted by a clock synchronized to the clock 308, by measuring the time of receipt of the signal from the sensor (likely the time of its peak magnitude), the location of the sensor 302 relative to the location of transducers of the array (and thus the frame image) can be determined by straight forward velocity/time calculations. In the present representative embodiment, the x,y coordinates of the sensor 302 (or x,y,z coordinates for volumetric imaging) are known relative to the n+1 transducer, the location of which is mapped to a coordinate system of the resultant first frame image. As such, the processor of the console/control unit determines the position of the sensor 302, and superposes the position on the frame image by executing instructions stored in the memory.

As noted above, processor 306 can be configured to transmit varying types of signal; namely the whole RF sensor frame, a clipped portion of the data, or a computed location of the sensor. Any combination of the above is also possible.

In the latter embodiment, the frame and line trigger signals are provided to the medical device for storage in the memory 307. In this representative embodiment, the memory 307 stores instructions executed by the processor to determine the location of the sensor 302 relative to the frame and line triggers. The data for the location of the sensor 302 are then transmitted (again, wirelessly) to the console/control unit so the location can be superposed on the particular frame image in real time.

An interventional medical device, such as a needle, an endoscope or endoscopic instrument, may be used to operate an end-effector in an internally situated area of interest of an object, such as a patient. As discussed above, it is possible to identify and track the medical device using ultrasound-guided procedures by attaching a miniaturized ultrasound sensor to the medical device, and analyzing the ultrasound data received by the sensor as the imaging probe insonifies the medium. For example, the ultrasound sensor may be located at or near a distal end (e.g., the tip) of the medical device, and thus be used to identify the precise localization of the distal end, which is desirable in many applications.

Generally, according to various embodiments, the sensor for tracking the position of the interventional medical device may be passive or active. This may be accomplished by detecting an ultrasonic wave impinging on the sensor, which is attached to the interventional medical device, and wirelessly transmitting information about this acoustic event to the console (e.g., wireless transceiver 209 of control unit 201) of the imaging system. Generally, passive sensors convert received ultrasonic signals into corresponding electrical signals, which are detected by external receivers, such as the wireless transceiver 209 of the control unit 201 in FIG. 2. Active ultrasound sensors likewise convert received ultrasonic signals into corresponding electrical signals, but then take active steps to transmit the electrical signals to external receivers, such as the wireless transceiver 209 or a receiver located in the handle or hub of the medical device to which the sensor is attached, such as wireless transceiver 312 in hub 304 in FIG. 3 (via electrical or optical conductors 303 or via a medical device wireless transceiver (not shown)). Notably, in an embodiment, the wireless transceiver 312 may be used as the receiver receiving RF signals from the passive ultrasound sensor, as well.

In an embodiment including a passive sensor attached to the interventional medical instrument, energy in ultrasonic waves (acoustic pulse) hitting an ultrasound transducer is harvested, and the harvested energy is used to enable transmission of a corresponding RF signal (RF pulse) to an external receiver. The RF signal contains information of the acoustic event (i.e., conversion of an acoustic wave to a corresponding RF signal).

Figure 5:
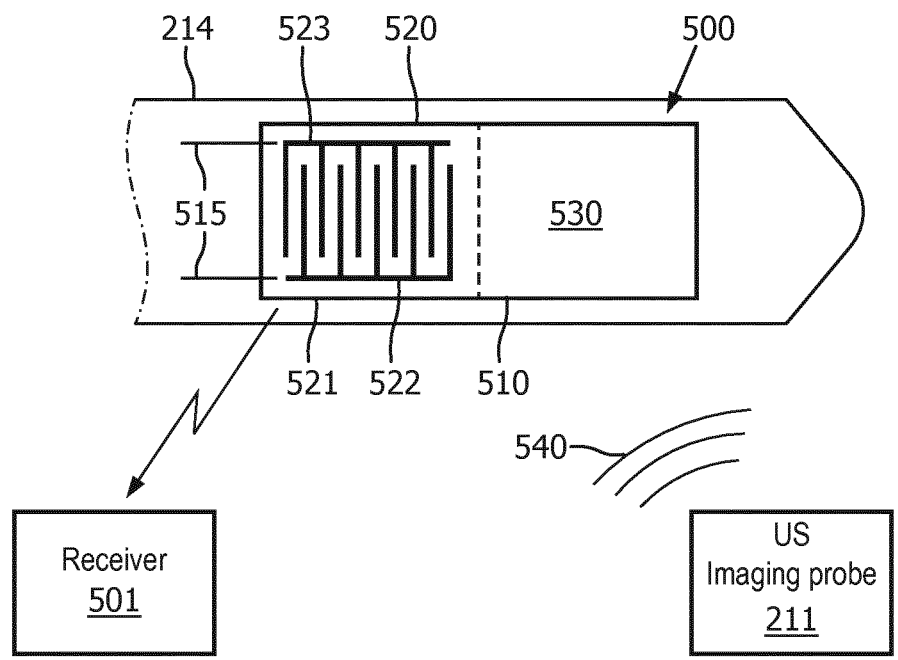
FIG. 5 is a conceptual diagram depicting a passive ultrasound transducer that harvests energy, according to a representative embodiment.

FIG. 5 is a conceptual diagram depicting an ultrasound transducer in a passive sensor that harvests energy, according to a representative embodiment. Referring to FIG. 5, sensor 500 comprises a small radio frequency identification (RFID) chip 510 and antennae 515. The sensor 500 is shown attached to the medical device 214 for purposes of illustration. Information is transmitted by the RFID chip 510 by to a wireless receiver 501 via the antennae 515. In various configurations, the receiver 501 may be implemented as the wireless transceiver 209 in the control unit 201. Conventionally, the transmitted information may be a stored bit sequence; however, in the depicted embodiment, the RFID chip 510 transmits an RF signal (sensor signal) related to the state of the sensor 500 (indicating an acoustic event) rather than a bit sequence. The sensor 500 in this case may be a structure that converts an incoming acoustic wave into a surface acoustic wave entering the RFID chip 510, as discussed below.

More particularly, the ultrasound imaging probe 211 transmits ultrasonic waves (acoustic pulses) 540 that are received by the RFID chip 510, and the energy in the ultrasound waves 540 is harvested to power the RFID chip 510. The RFID chip 510 then transmits the RF signal related to the state of the sensor 500 to the receiver 501. The timing of when the ultrasonic waves 540 hit the RFID chip 510 (and are transformed to corresponding RF signals) is known. Accordingly, the location of the RFID chip 510, and thus the location of the sensor 500, may be determined within the area of interest of the object (e.g., by the processor 205 executing a signal processing algorithm) based on delay between an ultrasonic wave hitting the RFID chip 510 and receipt of the corresponding RF signal. In other words, the location of the sensor 500 is determined based on a known delay between the ultrasonic waves 540 hitting the sensor 500 and the receiver 501 receiving the corresponding electrical signal, as well as known information about a transmit pattern of the ultrasound imaging probe 211.

In the depicted embodiment, the RFID chip 510 includes a surface acoustic wave (SAW) resonator 520 and a transition area 530. The SAW resonator 520 is an electronic resonator circuit tuned to a specific resonance frequency for converting ultrasonic waves to electrical RF signals, enabling the SAW resonator 520 to harvest the energy from the ultrasonic waves 540 that match the resonance frequency. The SAW resonator 520 also converts the ultrasonic waves 540 to corresponding RF signals that are transmitted to or otherwise detected by the receiver 501. That is, the energy in the ultrasonic waves 540 hitting the ultrasound sensor 500 is harvested, and used to transmit RF signals, converted by the SAW resonator 520 and containing information of the acoustic event, to the receiver 501.

The transition area 530 of the RFID chip 510 performs mode conversion, transforming the longitudinal ultrasonic waves 540 (acoustic pulses), e.g., received from the ultrasound imaging probe 211, to corresponding surface acoustic waves that resonate the SAW resonator 520. This mode conversion occurs when the ultrasound energy impacts a surface of the interface area at an angle steeper than a certain critical angle, as would be apparent to one skilled in the art. As the SAW resonator 520, along with the transition area 530, may be a foil-like structure, it can be shaped such that the transition area 530 is oriented appropriately relative to the impinging ultrasonic waves 540 for mode conversion to surface acoustic waves to occur. Generally, mode conversion occurs when the ultrasonic waves encounter an interface between materials of different acoustic impedances, and the incident angle is not normal to the interface.

The SAW resonator 520 includes a piezoelectric layer 521 formed over a substrate (not shown), and an electrode layers 522 and 523 formed over the piezoelectric layer 521. The piezoelectric layer may be formed of any compatible piezoelectric material, such as lithium niobate (LiNbO$_3$) or aluminum nitride (AlN), and the electrode layer 522 may be formed of any compatible electrically conductive material, such as molybdenum (Mo) or tungsten (W), for example. In the depicted embodiment, the SAW resonator 520 is an Inter-Digital Transducer (IDT), in which the electrode layers 522 and 523 have an interleaving comb-like structure. The antennae 515 are attached to the IDT for transmission of the RF signals. Thus, the SAW resonator 520 converts the incident surface acoustic waves propagated from the transition area 530 into RF signals that are collected and transmitted to the receiver 501.

In another embodiment including a passive sensor, an external RF signal is continuously broadcast by an RF transmitter from an external antenna (or at least continuously broadcast over timespans where responses are expected based on previously detected sensor location.) The sensor includes an electronic resonator circuit tuned to the frequency of the external RF signal. The electronic resonator circuit has a local antenna and an ultrasound transducer with a resonance frequency, where the ultrasound transducer is capable of modulating and/or detuning the electronic resonator circuit in response to receiving the ultrasonic waves from the ultrasound imaging probe 211. When the electronic resonator circuit is within the nearfield of the external antenna (e.g., less than one tenth of the wavelength of the RF signal), it presents a modulated load to the external antenna, indicating when the ultrasound transducer converts an ultrasonic wave to a corresponding electrical RF signal. This modulated load on the external antenna can be detected by monitoring power levels going into the external antenna. For example, an increase in current drawn by the external antenna may indicate the presence of the modulated load resulting from resonation of the ultrasound transducer, although other indications may be used without departing from the scope of the present teachings. This embodiment may be based on a modification of passive RFID chips and/or capacitive micromachined ultrasonic transducer (CMUT) devices operating in the lower RF ranges, which may be any RF signal with frequency less than about 100 MHz (e.g., 120 kHz-150 kHz or 13.56 MHz). The nearfield for 100 MHz would be about 30 cm, for example.

Figure 6A:
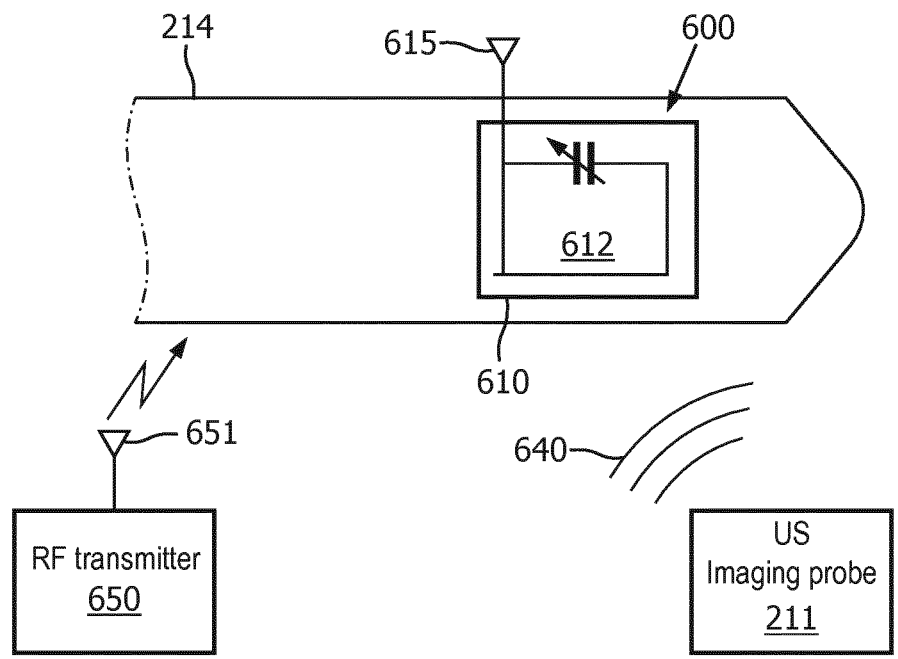
FIG. 6A is a conceptual diagram depicting a passive ultrasound sensor that receives a continuously broadcast, lower frequency RF signals from an RF transmitter via an external antenna, according to a representative embodiment.
Figure 6B:
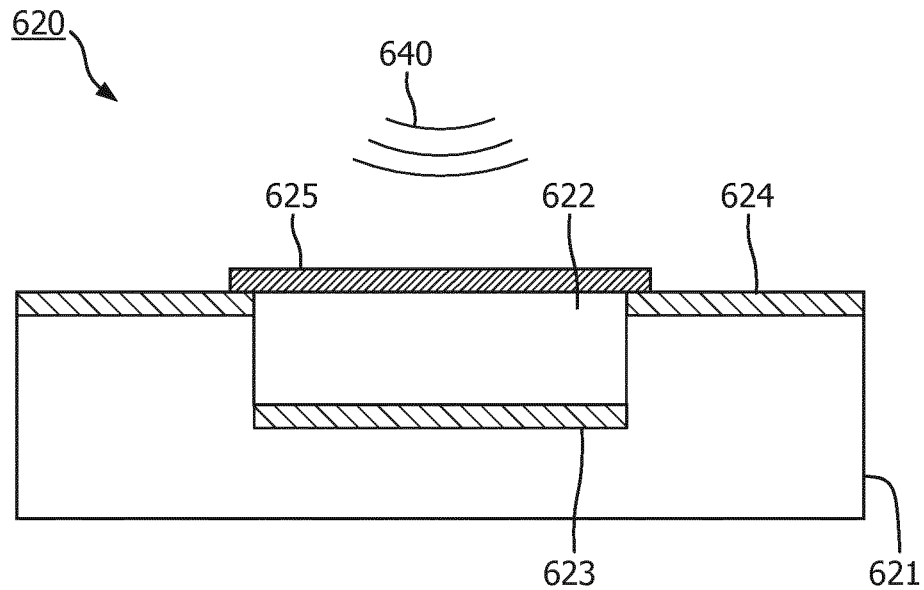
FIG. 6B is a conceptual diagram depicting a capacitive micromachined ultrasonic transducer (CMUT) that may be incorporated as a passive ultrasound sensor, according to a representative embodiment.

FIGS. 6A and 6B are conceptual diagrams depicting a passive sensor that receives continuously broadcast external RF signal from an RF transmitter 650 (sometimes referred to as external transmitter 650) via an external antenna 651 remote from the medical device 214, according to a representative embodiment. The RF transmitter 650 may be included in the control unit 201 or the hub 304, for example, or may be a separate device.

Referring to FIG. 6A, passive sensor 600 comprises an electronic resonator circuit 610 tuned to the frequency of the external RF signal from the external antenna 651, and includes a capacitive element 612 (i.e., an ultrasound transducer), and an antenna 615 (sometimes referred to as local antenna 615) attached to the interventional medical device 214. Alternatively, the interventional medical device 214 may be used as the antenna (eliminating the need for the antenna 615), and the RF transmitter 650 could still be used to detect modulated load when placed at a sub-wavelength, nearfield distance, as discussed above. The capacitive element 612 in the electronic resonator circuit 610 may be a passive CMUT device or CMUT-like device, for example, as shown in FIG. 6B. A CMUT is an ultrasound transducer in which the energy transduction between acoustic and electrical signals occurs due to change in capacitance. It is understood that a CMUT-like device has a capacitance that changes slightly according to pressure from an acoustic wave hitting it. The capacitive element 612 is able to sense the ultrasonic waves 640, and modulates and/or detunes the electronic resonator circuit 610 in response. That is, the ultrasound sensor 600 is basically a capacitive micromachined microphone for ultrasound frequencies. The capacitive element 612 is modulated by the ultrasonic waves 640 from the ultrasound imaging probe 211. The membranes in a CMUT-like device can be implanted with charge so they attract each other and make the capacitive modulation due to ultrasound more pronounced.

FIG. 6B is a simplified cross-sectional view of an illustrative CMUT 620, which may be incorporated as the capacitive element 612 in the electronic resonator circuit 610 of FIG. 6A, providing a CMUT-like device. The CMUT 620 includes substrate 621 forming a cavity 622. Active electrode 623 is formed at the bottom of the cavity 622, and ground electrode 624 is formed on an upper surface of the substrate 621 around (or on either side of) the cavity 622. A vibrating membrane 625 is connected to the ground electrode 624 across the cavity 622, enabling the vibrating membrane 625 to oscillate in response to received ultrasonic waves 640. Generally, a bias voltage is applied over the active and ground electrodes 623 and 624, respectively, and the oscillation of the vibrating membrane 625 converts the ultrasonic waves 640 to an electrical RF current signal output at the activating electrode 623. However, in the present embodiment, the bias voltage is not needed, and the signal may consist of a change in capacitance leading to a change in the resonance frequency of passive sensor 600 as detected by RF transmitter 650.

Continuous transmission of lower frequency RF signals (e.g., less than about 100 MHz) from the RF transmitter 650 may be performed at fixed frequency to which the frequency of the electronic resonator circuit 610 is initially tuned. The RF transmitter 650 is thus able to detect loading of the external antenna 651 caused by the modulation loading and/or detuning of the electronic resonator circuit 610 in response to the ultrasound sensor 600 receiving ultrasonic waves 640 from the ultrasound imaging probe 211. Because the measurement of the modulation signal is performed at the RF transmitter 650 side (based on detection of antenna loading), there is no need to receive and/or process reflected or transmitted RF signals from the ultrasound sensor 600. Thus, transmission of the RF signal from the external antenna 651 need not be interrupted for receiving RF signals, and so the modulation can be measured continuously. Accordingly, the location of the passive sensor 600 within the area of interest of the object may be determined (e.g., by the processor 205 executing a signal processing algorithm) based on delay between an ultrasonic wave hitting the electronic resonator circuit 610 and detection of loading of the external antenna 651.

In another embodiment including a passive sensor, an external RF signal is continuously broadcast by an RF transmitter from an external antenna, as mentioned above, where the external antenna is remote from the passive sensor. The passive sensor includes an electronic resonator circuit tuned to the frequency of the external RF signal. The electronic resonator circuit has an attached local antenna, and includes an ultrasound transducer (ultrasound sensor) having a resonate cavity that modulates and/or detunes the electronic resonator circuit when resonating at its resonance frequency in response to received ultrasonic waves.

The electronic resonator circuit is configured in combination with the local antenna, such that a reflection signal of the illuminating external RF signal is created at a frequency of a higher harmonic. Therefore, the higher harmonic reflection signal may be detected using an external RF receiver. Thus, transmission of the external RF signal from the external antenna need not be interrupted to receive the reflection signal, and so modulation of the passive sensor can be measured continuously. When ultrasonic waves hitting the sensor change the capacitance, the resonating circuit detunes, and thus the amplitude of resonance due the continuous broadcasting RF transmitter reduces. This, in turn, also reduces the reflected harmonic signal that is continuously received, i.e. the ultrasound modulation of the capacitive element leads to an amplitude modulation of the received harmonic reflection. The electronic resonator circuit works in the farfield of the external antenna (e.g., greater than one tenth of the wavelength of the RF signal), and at a frequency significantly higher that the ultrasound frequency of the imaging probe.

Figure 6C:
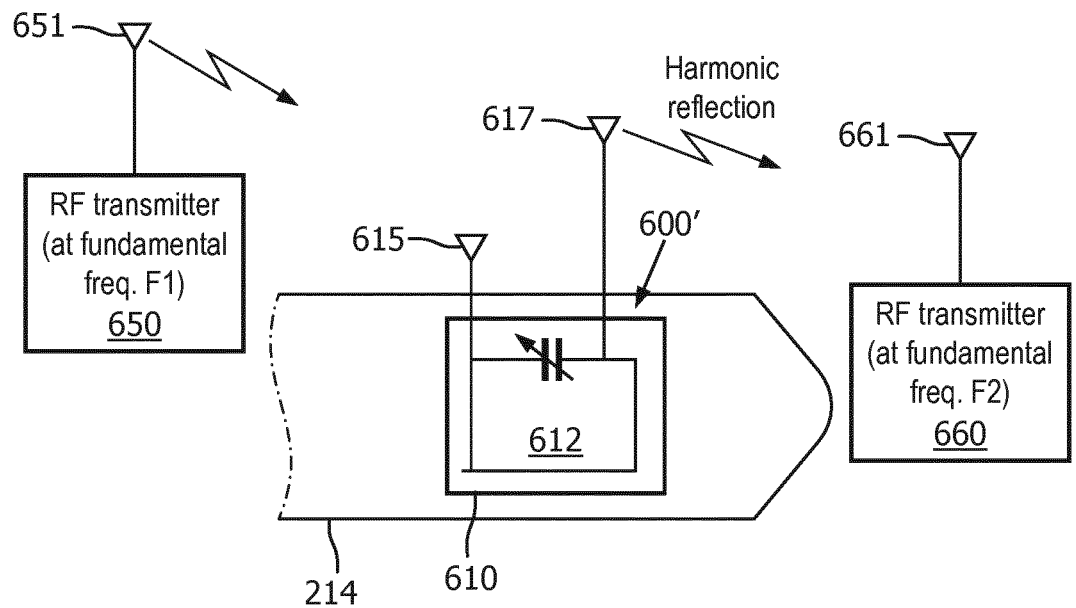
FIG. 6C is a conceptual diagram depicting a passive ultrasound sensor that receives a continuously broadcast external RF signal at first fundamental frequency, and reflects a harmonic signal at second fundamental frequency, according to a representative embodiment.

More particularly, FIG. 6C is a conceptual diagram depicting a passive sensor that receives continuously broadcast external RF signal at first fundamental frequency F1, and reflects a harmonic signal at second fundamental frequency F2, according to a representative embodiment.

Referring to FIG. 6C, passive sensor 600' comprises electronic resonator circuit 610, which includes a capacitive element 612 (i.e., an ultrasound transducer) and receive local antenna 615 and transmit local antenna 617. The electronic resonator circuit 610 is tuned to receive the RF signal from the RF transmitter 650 and transmitter antenna 651 at the first fundamental frequency F1, via the receive local antenna 615, and to transmit the harmonic reflection RF signal to the receiver antenna 661 and RF receiver 960 at the second fundamental frequency F2, via the transmit local antenna 617. The RF transmitter 650 and/or the RF receiver 660 may be included in the control unit 201 or the hub 304, for example, or may be separate devices. As stated above, the harmonic reflection signal of the RF signal is created at a higher harmonic frequency, such that the second fundamental frequency F2 is greater than the first fundamental frequency F1. Therefore, the higher harmonic reflection signal may be detected by the external RF receiver 660. Thus, transmission of the RF signal from the external RF transmitter 650 need not be interrupted for reception of the harmonic reflection signal, and modulation of the passive sensor 600' can be measured continuously.

In contrast to the passive sensors, discussed above, the wireless ultrasound sensor may be an active sensor. In an embodiment including an active sensor attached to the interventional medical instrument, energy in ultrasonic waves (acoustic pulse) hitting an ultrasound transducer is harvested, as discussed above with reference to FIG. 5, and the harvested energy is used to transmit an electrical RF signal, containing information of the acoustic event, to an active (e.g., battery powered) circuit in or near the handle or hub (such as hub 304) of the interventional medical device. The battery powered active circuit may include a receiver, an amplifier and a transmitter, for example. Thus, the active circuit is able to amplify the received RF signal, which is used to modulate a high frequency RF signal transmitted from the hub or handle of the medical device to the control unit 201 (e.g., via the wireless transceiver 209).

Figure 7:
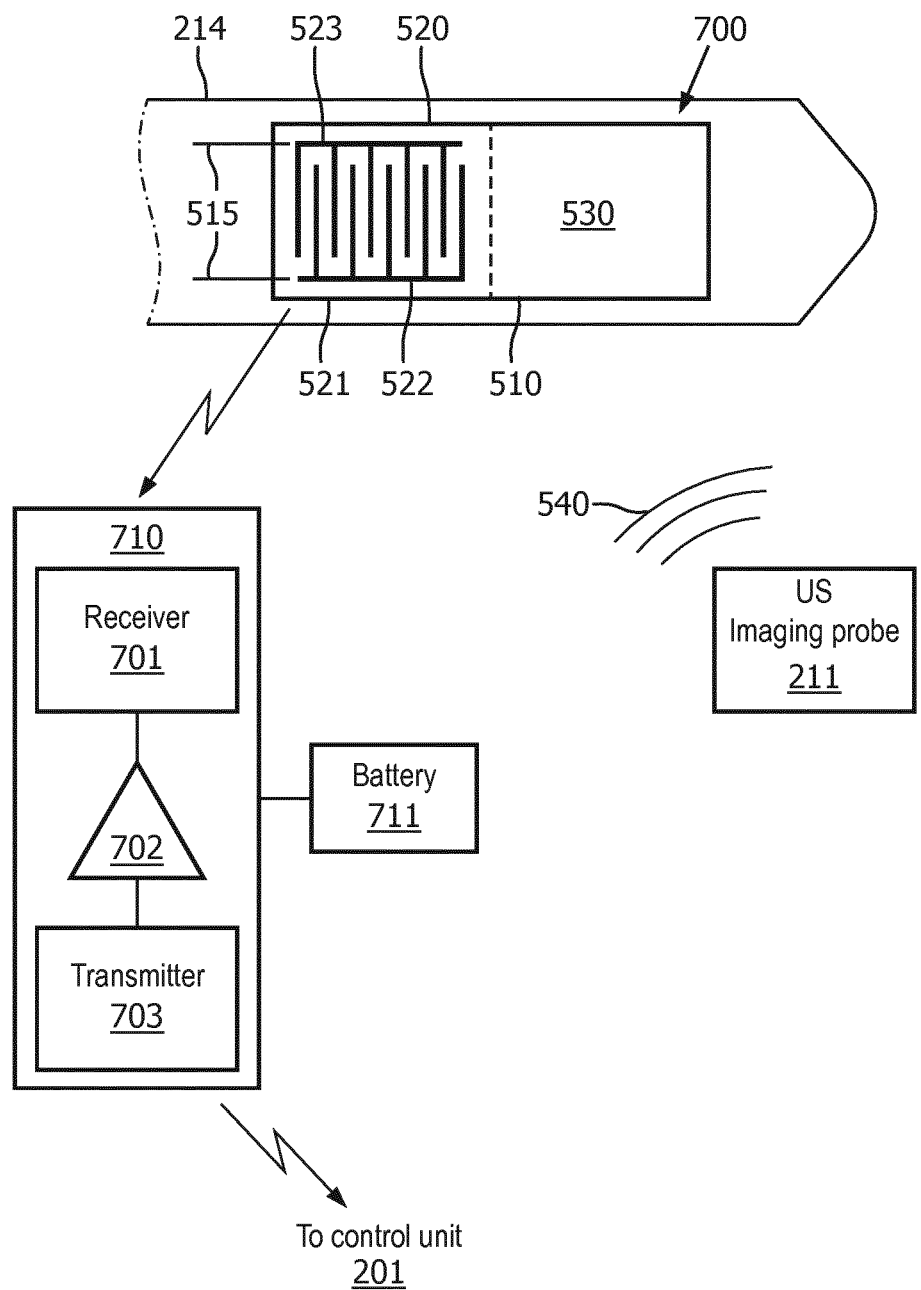
FIG. 7 is a conceptual diagram depicting an active sensor that harvests energy to send an RF signal for active retransmission, according to a representative embodiment.

FIG. 7 is a conceptual diagram depicting an ultrasound transducer in an active sensor that harvests energy to send an RF signal for active retransmission, according to a representative embodiment. Referring to FIG. 7, sensor 700 includes some of the same components as in sensor 500, discussed above with reference to FIG. 5, in which case the same reference numerals are used. The sensor 700 comprises a small RFID chip 510 and antennae 515. The sensor 700 is shown attached to the medical device 214 for purposes of illustration. Information is transmitted by the RFID chip 510 to a wireless receiver 701 in active circuit 710 (e.g., repeater) via the antennae 515, where the active circuit 710 is located in the handle or hub 304 of the medical device 300 (although not shown in FIG. 3). The active circuit 710 also may include an amplifier 702 for amplifying the received RF signal and a transmitter 703 for wirelessly transmitting the amplified RF signal to the wireless transceiver 209 in the control unit 201. The active circuit 710 efficiently transmits the RF signal (data) it receives from the sensor 700 to the control unit 201. Since the active circuit 710 has an active power source, e.g., battery 711, it can operate at high frequencies (e.g., greater than about 200 MHz) to maximize antenna efficiency. Of course, other means of providing power to the active circuit 710 may be incorporated without departing from the scope of the present teachings.

In an embodiment, the received RF signal may be provided from the receiver 701 to the signal conditioning module 305, which includes the amplifier 309, filter 310, and digitizer 311, before being provided to the transmitter 703 for wireless transmission. In this case, the functionality of the amplifier 702 may be replaced by that of the amplifier 309 in the signal conditioning module 305. In another embodiment, the receiver 701 and the transmitter 703 may be replaced by a transceiver that receives at a lower and transmits at a higher frequency. In sum, the RFID chip 510, powered by harvested energy, transmits an RF signal related to the state of the sensor 700 (indicating an acoustic event). This RF signal is received, amplified and retransmitted by the active circuit 710 (effectively acting as a repeater) to the control unit 201.

As discussed above, the ultrasound imaging probe 211 transmits ultrasonic waves (acoustic pulses) 540 that are received by the RFID chip 510, and the energy in the ultrasonic waves 540 is harvested to power the RFID chip 510. The RFID chip 510 then transmits the RF signal related to the state of the sensor 700 to the active circuit 710, for amplification and transmission to the control unit 201. The timing of when the ultrasonic waves 540 hit the RFID chip 510 (and are transformed to corresponding RF signals) is known. Accordingly, the location of the RFID chip 510, and thus the location of the sensor 700, may be determined within the area of interest of the object (e.g., by the processor 205 executing a signal processing algorithm) based on delay between an ultrasonic wave hitting the RFID chip 510 and receipt of the corresponding RF signal. In other words, the location of the sensor 700 is determined based on a known delay between the ultrasonic waves 540 hitting the sensor 700 and the receiver 701 receiving the corresponding electrical signal, as well as known information about a transmit pattern of the ultrasound imaging probe 211. It is understood that the other passive sensors discussed above, e.g., including passive sensor 600 in FIGS. 6A and 6B, may be incorporated in place of the sensor 700 in the depicted embodiment, without departing from the scope of the present teachings.

If the interventional medical device 214 is a needle, for example, a SAW-based sensor, such as sensor 500 or 700, may be located near the tip of the needle, and the needle itself may be used as the antenna (e.g., instead of antennae 515). The wireless receiver 701 may be in direct or close contact to the needle at the proximal end to pick up the sensor signal efficiently. The received data can be used to modulate an RF wave of much higher frequency than the sensor signal (to allow sufficient modulation depth to capture the bandwidth of the sensor signal). This high frequency RF signal can then be amplified by the amplifier 702 and efficiently transmitted wirelessly by the transmitter 703 using a smaller antenna (due to the high frequency).

An advantage of the receiver 701 being in close contact, as opposed to direct contact, with the needle is that no on-needle interconnect is needed. However, the increased range and sensitivity provided by an active RF transmitter (transmitter 703) can still be leveraged. Also, because the receiver 701 and the active transmitter 703 do not have to be in direct contact with the medical device 214, but merely in close proximity, the active circuit 710 is easier to provide as a separate non-disposable part. For example, the hub may be reusable, such that the hub clips onto the end of a needle. Because the communication with the sensor 700 via the needle is wireless, there is no electrical connector required, thereby decreasing disposable device cost and reliability issues. In an embodiment, the reusable hub may be made in a patch form-factor, for example, that can be adhered to the surface of the object (e.g., the skin of the patient) close to the region of interest.

Also, the bandwidth of the sensor signal from the sensor 700 can be reduced using an envelope detector (not shown), for example. An illustrative analog manner for implementing the envelope detector is to use an analog multiplier to square the sensor signal. This creates frequency shifted components near DC and double the carrier frequency. A low pass filter isolates the low frequency components representing a crude envelope detector, to provide a signal with much lower bandwidth.

In another embodiment including an active wireless sensor, the sensor on interventional medical device may be connected by wires to an active circuit in the hub and/or handle of the medical device. The active circuit is optimized to efficiently extract data from the sensor, and the received signal may be used to modulate a high frequency RF signal transmitted from the hub and/or handle to the control unit 201 of the console.

Figure 8:
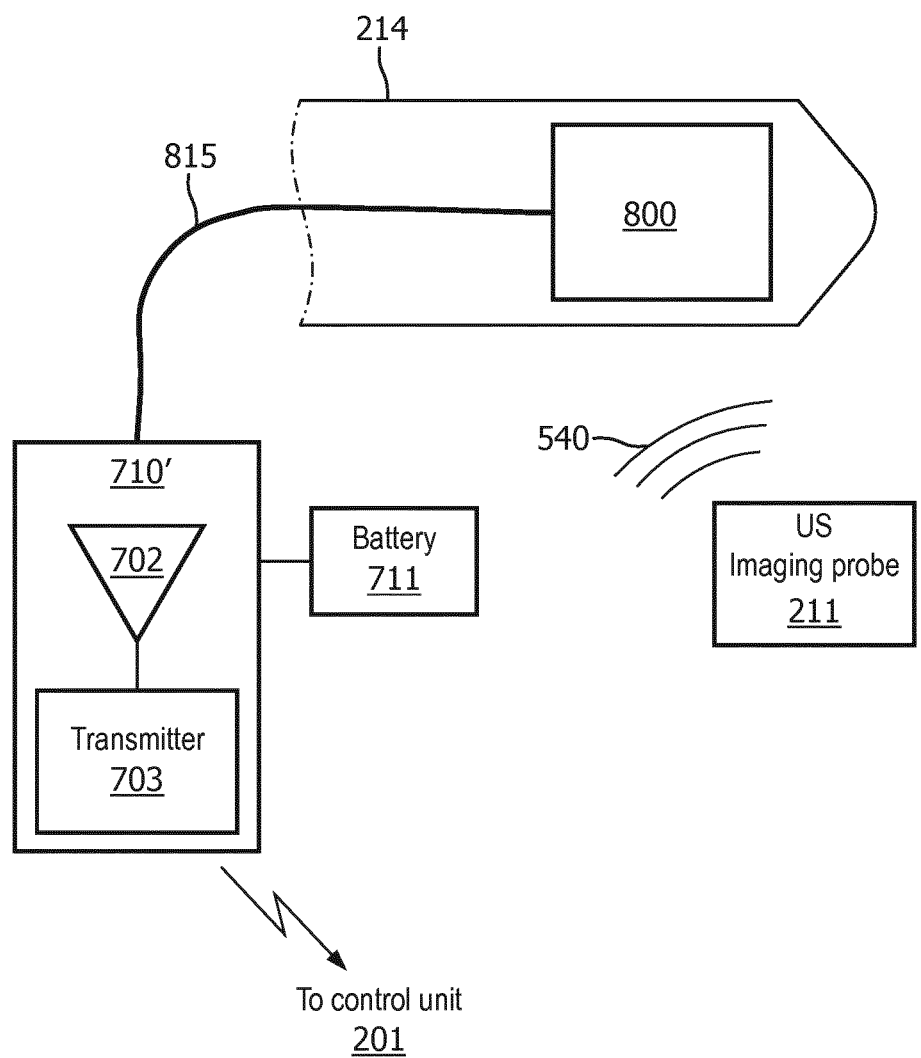
FIG. 8 is a conceptual diagram depicting an active sensor that sends an RF signal for active retransmission via wires, according to a representative embodiment.

FIG. 8 is a conceptual diagram depicting an ultrasound transducer in an active sensor that sends an RF signal for retransmission via wires, according to a representative embodiment. Referring to FIG. 8, some of the components are the same as those in FIG. 7, discussed above, in which case the same reference numerals are used. In this embodiment, the medical device 214 may be needle shaped, or otherwise elongated, with ultrasound sensor 800 located near the tip. The ultrasound sensor 800 is connected to active electronics, such as the active circuit 710', through one or more miniature wires 815 running along the needle-like medical device 214. The miniature wires 815 may run internally or externally along the medical device 214, without departing from the scope of the present teachings. The active circuit 710' is located in the handle or hub 304 of the medical device (although not shown in FIG. 3). The active circuit 710' includes amplifier 702 for amplifying the received RF signal and a transmitter 703 for wirelessly transmitting the amplified RF signal to the wireless transceiver 209 in the control unit 201. No wireless receiver 701 is needed. To reduce the bandwidth of the RF signal that is transmitted by transmitter 703, an analog envelope detection may be performed e.g., by amplifier 702 as described above. When the ultrasound sensor 800 is small, it may have low sensitivity and produce a signal that is easily corrupted by transfer over the interconnect (including wire(s) 815) of the medical device 214. Thus, care must be taken on how to robustly extract the RF signal from the sensor through the medical device 214 interconnect (e.g., needle interconnect), and active electronics offers opportunity to do so.

For example, assuming for purposes of discussion that the ultrasound sensor 800 functions like a miniature condenser microphone that has a varying capacitance as the ultrasonic wave perturbs its membrane, as discussed above with reference to FIGS. 6A and 6B, for example. In this case, the ultrasound sensor 800 may be made part of an electronic resonator circuit that FM modulates a high frequency oscillation. This signal is then amplified (e.g., by the amplifier 702) and directly transmitted (e.g., by the transmitter 703) via the miniature antenna in the handle or hub (e.g., hub 304).

If the ultrasound sensor 800 is polyvinylidene fluoride (PVDF) based, for example, it can not drive a capacitive load. In this case, the active electronics in the hub will function as a charge amplifier. This keeps the voltage over the interconnect constant to eliminate parasitic interconnect capacitance influence, while measuring the sensor currents that the acoustic signal generates. Once the sensor signal is efficiently extracted in the hub, the power source in the hub (e.g., battery 711) can be leveraged to create a strong wireless transmission that uses higher frequencies, enabling the use of small footprint antennas with high efficiency.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for performing a medical procedure in a region of interest of a patient, the system comprising:
    an interventional medical device insertable into the region of interest;
    a passive sensor attached to a portion of the interventional medical device, the passive sensor configured to convert an ultrasonic wave received from an ultrasound imaging probe to a corresponding electrical radio frequency (RF) signal,
    wherein the passive sensor comprises:
        (i) a radio frequency identification (RFID) chip configured to convert the ultrasonic wave to the RF signal, wherein the converted RF signal is generated to contain information indicating the conversion from the ultrasonic wave, the RFID chip comprising:
            a transition area configured to perform mode conversion that transforms the ultrasonic wave, which is a longitudinal ultrasound wave, to a corresponding surface acoustic wave, and
            a surface acoustic wave (SAW) resonator having an electronic resonator circuit tuned to a resonance frequency, the SAW resonator configured to convert the corresponding surface acoustic wave to the RF signal by resonating the SAW resonator at the resonance frequency, and
        (ii) a local antenna configured to transmit the RF signal external to the region of interest of the patient;
    an RF receiver located external to the region of interest of the patient, the RF receiver configured to detect the RF signal transmitted by the local antenna of the passive sensor; and
    a processor configured to determine a location of the passive sensor within the region of interest based on a delay between (i) receipt of the ultrasonic wave at the RFID chip and (ii) detection of the RF signal by the RF receiver.

2. The system of claim 1, wherein the location of the passive sensor is determined based on the delay and information about a transmit pattern of the ultrasound imaging probe.

3. The system of claim 1, wherein the SAW resonator is configured to harvest energy from the corresponding surface acoustic wave when resonating at the resonance frequency, and wherein the harvested energy powers the RFID chip.

4. The system of claim 1, wherein the SAW resonator is shaped such that the transition area is oriented to perform the mode conversion that transforms the ultrasonic wave to the corresponding surface acoustic wave.

5. The system of claim 1, wherein the SAW resonator includes a piezoelectric layer formed over a substrate and at least one electrode layer formed over the piezoelectric layer.

6. The system of claim 5, wherein the SAW resonator comprises an Inter-Digital Transducer (IDT), in which the at least one electrode layer comprises an interleaving comb-like structure, and the local antenna is attached to the IDT.

* * * * *